United States Patent [19]
Farina et al.

[11] Patent Number: 6,033,107
[45] Date of Patent: Mar. 7, 2000

[54] TEMPERATURE MAPPING SYSTEM

[75] Inventors: Dino J. Farina, Waltham; Henry A. Lyden, Wellesley, both of Mass.

[73] Assignee: Temptronic Corporation, Newton, Mass.

[21] Appl. No.: 09/115,216

[22] Filed: Jul. 14, 1998

Related U.S. Application Data

[60] Provisional application No. 60/052,558, Jul. 15, 1997.

[51] Int. Cl.[7] .............................. G01N 25/58; G01K 11/20
[52] U.S. Cl. .................................................. 374/5; 374/161
[58] Field of Search .................... 374/4, 5, 6, 7, 374/15, 161, 137, 112, 162

[56] References Cited

U.S. PATENT DOCUMENTS

| | | | |
|---|---|---|---|
| 4,439,049 | 3/1984 | Hoogendoorn et al. | 374/5 |
| 4,466,746 | 8/1984 | Hancock et al. | 374/5 |
| 5,032,727 | 7/1991 | Cox, Jr. et al. | 374/5 |
| 5,173,868 | 12/1992 | Kalley et al. | 374/121 |
| 5,711,603 | 1/1998 | Ringermacher et al. | 374/5 |
| 5,718,511 | 2/1998 | Mundt | 374/137 |
| 5,816,703 | 10/1998 | Yamazaki et al. | 374/5 |
| 5,834,661 | 11/1998 | Nonaka et al. | 374/5 |
| 5,902,044 | 5/1999 | Pricer et al. | 374/137 |

FOREIGN PATENT DOCUMENTS

| | | | |
|---|---|---|---|
| 0127660 | 5/1987 | Japan | 374/4 |
| 4051027212 | 4/1993 | Japan | 374/4 |

OTHER PUBLICATIONS

Syed et al. Thermographic Detection of Corrosion in Aircraft Skin, NASA Langsley Recearch Center.
Thermal Map 2. A new generation in advanced real time wafer temperature measurement systems. Sens Array Corp., 1996.
Temptronic Corporation, *User's Guide to ThermoMap*, software version 2.0, Rev A, Jun. 1997.
Temptronic Corporation, *LabView Block Diagrams for the ThermoMap Hot–Spot Detector*, Jul., 1997.

*Primary Examiner*—G. Bradley Bennett
*Assistant Examiner*—Gail Verbitsky
*Attorney, Agent, or Firm*—McDermott, Will & Emery

[57] ABSTRACT

A method of and system for determining the location of hot spots on the surface of an object which has thermotropic material applied to the surface are disclosed. The system is designed to varying the nominal temperature of the object through a range of nominal temperatures between a first nominal temperature limit and a second nominal temperature limit, wherein one temperature limit is below and the other nominal temperature limit is above the temperature at which the thermotropic material changes phase. A sequence of images of the surface are acquired, each of the images depicting a two dimensional temperature representation of the surface at a predetermined nominal temperature within the range of nominal temperatures, wherein each image in the sequence represents an incremental change in nominal temperature than that of a preceding image. Select ones of the images are processed to define the intensity signature of valid hot spots in the select ones of the images and to determine the location of the hot spots on the surface as a function of the defined intensity signature.

40 Claims, 2 Drawing Sheets

TEMPERATURE MAPPING SYSTEM

CROSS-REFERENCE TO RELATED APPLICATIONS

The present application is based on provisional application, U.S. Ser. No. 60/052,558, filed on Jul. 15, 1997.

STATEMENT REGARDING FEDERALLY SPONSORED RESEARCH

Not Applicable

REFERENCE TO MICROFICHE APPENDIX

Not Applicable

FIELD OF THE INVENTION

The present invention relates to temperature measurements, and more particularly to systems for and methods of determining and indicating the temperature characteristics of an object so as to derive a high resolution, two dimensional graphic representation of the surface temperature of the object.

BACKGROUND OF THE INVENTION

It is important for designers and manufacturers to have accurate knowledge of the surface temperature of a monolithic integrated circuit (hereinafter referred to as IC). The presence of "hot spots" on the surface of an IC may create reliability and performance problems. If the location of such hot spots are known with high resolution, designers may be able to modify the IC layout to optimize dissipation or mitigate the problem via other techniques known to those in the art.

Prior art methods of mapping the surface temperature of an IC include infrared thermography and the use of an array of temperature sensitive elements such as thermocouples, thermistors, RTD's, and bipolar junction sensors. Such prior art methods typically suffer from poor spatial resolution.

Prior art methods have used nematic liquid crystals (hereinafter referred to as NLCs) as a means for locating hot-spots on ICs and mapping the surface temperature of an IC. However, these previous computerized analytical methods have had limited success due primarily to their inability to reliably discriminate between actual hot-spots on the IC, the background features of the IC substrate and the potentially spurious behavior and visible internal artifacts associated with NLC materials. These prior art NLC methods have also experienced poor spatial resolution, and non-repeatable results.

Since modem IC's are typically fabricated on a sub-micron scale, low resolution temperature mapping makes it difficult to resolve and isolate the occurrence of nearly-adjacent IC hot spots using prior art techniques.

It is an object of this invention to provide a temperature mapping system and method which significantly overcomes the aforementioned problems inherent in the prior art.

It is another object of this invention to provide a temperature mapping system which provides spatial resolution sufficient to detect and resolve nearly-adjacent hot spots on the surface of an IC.

SUMMARY OF THE INVENTION

The method and system of the present invention is for determining the location of hot spots on the surface of an object. In one embodiment this is achieved by applying a thermotropic material to the surface of the object; varying the nominal temperature of the object through a range of nominal temperatures between a first nominal temperature limit and a second nominal temperature limit, wherein one temperature limit is below and the other nominal temperature limit is above the temperature at which the thermotropic material changes phase; acquiring a sequence of images of the surface, each of the images depicting a two dimensional temperature representation of the surface at a predetermined nominal temperature within the range of nominal temperatures, wherein each image in the sequence represents an incremental change in nominal temperature than that of a preceding image; and processing select ones of the images to define the intensity signature of valid hot spots in the select ones of the images and to determine the location of the hot spots on the surface as a function of the defined intensity signature.

In another embodiment the nominal temperature of the object is varied in incremental steps so that the object is stabilized at each of the nominal temperatures when each of the images of the surface are acquired.

In another embodiment the user selects the images he/she wishes to process to determine the hot spots.

In another embodiment, when defining the intensity signature of valid hot spots the potential hot spots are detected in each of the select ones of the images.

In yet another embodiment each of the selected images is represented by a plurality of pixels, each of the pixels of a determinable intensity, and the potential hot spots in each of the select ones of the images are detecting by, at least in part, binarizing a plurality of the pixels within each of the select images such that each pixel is designated as either a hot-spot pixel or a non-hot-spot pixel.

In still another embodiment, the potential hot spots in each of the select ones of the images is defined at least in part by applying a smoothing filter to a plurality of regions within each of the selected images prior to the step of binarizing the plurality of the pixels.

In yet another embodiment, a low-pass spatial filter is applied to a plurality of regions within each of the images after binarizing the plurality of the pixels.

And in still another embodiment, when binarizing a plurality of pixels each of the pixels are compared to a predetermined threshold range and each of the pixels are designated as a hot-spot pixel if the pixel falls within the threshold range and designating the pixel as a non-hot-spot pixel if the pixel does not fall within the threshold range.

And in yet another embodiment each potential hot-spot is verified.

In still another embodiment, each potential hot-spot is verified by, at least in part, (i) comparing consecutive images of the select ones in the sequence in which they are acquired, and (ii) eliminating hot-spot pixels not having a hot-spot pixel at a corresponding location in an immediately succeeding image.

Yet another embodiment verifies each potential hot spot by, at least in part, adding pixels from corresponding locations of each of the select images to produce a resulting pixel corresponding to an integer value representative of the number of images having hot-spot pixels at the corresponding location so as to produce the two dimensional graphic temperature representation.

In another embodiment, the resulting pixel includes one of a plurality of integer values, each of the integer values corresponding to an assigned temperature and being represented by a predetermined color.

Yet in another embodiment the object is maintained at a first nominal temperature, and the surface is viewed through a crossed polarizing filter and video data representative of a polarized image of the surface is produced prior to applying the thermotropic material.

In still another embodiment the sequence of images are acquired by, at least in part, receiving and recording the polarized image at each of nominal temperatures so as to produce a time-series of images, and generating a thermal map of the surface from the time-series of images.

In another embodiment the object is secured to a temperature control platform, and the temperature of the object is controlled through the temperature control platform.

And in another embodiment the surface is viewed so as to receive and focus light received from the surface, so as to form an image, and the image is converted into a series of video data elements representative of the image.

And in yet another embodiment the thermotropic material applied to the surface is illuminated for each of the images.

In still another embodiment the sequence of images is acquired, at least in part, by receiving video data from an optics unit for each of the images; forming the video data into a frame representative of the image; and storing the video data of each of the frames so as to establish a data set representative of a time-sequence of the images.

In another embodiment the sequence of images is acquired by receiving each of the images and generating map data representative of a thermal map of the surface corresponding to variations in consecutive frames of the images; and receiving the map data and displaying the two dimensional graphic temperature representation from the map data.

And in another embodiment the images that are selected are determined by detecting the first image of the sequence that is determined to have a dark spot, and identifying a temperature corresponding to the first image, so as to determine the temperature at which the thermotropic material changes phase.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE INVENTION

The invention is directed to a method of and apparatus for mapping the surface temperature of an object, typically an electronic component, although the invention can be used with other objects. The invention uses optical and physical properties of a thermotropic material, e.g. the phase change of a NLC to derive a high resolution, two dimensional graphic representation of the surface temperature of the object.

The NLC is a stable, intermediate, or meso-thermodynamic phase between a pure solid and a pure liquid that some substances, usually organic in nature, can exhibit under specific environmental conditions. The NLC can result in these substances either from heating the solid phase or by cooling the liquid phase. Other forces such as mechanical shear and pressure, electric and magnetic fields and chemical reactions can also cause the phase change to occur, but the characteristic preferably used in the embodiment of the invention is the thermally induced or thermotropic process.

The NLC possesses some of the mechanical properties of a liquid (surface tension, viscosity and weak intermolecular bonds), and some of the optical properties of a crystalline solid (anisotropy to light, dichroism, and birefringence), but it is the combination of these properties that make the NLC useful to electronic component design engineers and failure analysts. Chief among these properties is the strong light polarizing capabilities that the NLC possesses.

A non-polarizing surface will appear dark when viewed through crossed polarizers, because such a filter will substantially block the non-polarized, reflected light. However, if the same non-polarizing surface is coated with a material exhibiting the NLC, the surface will appear bright when viewed through crossed polarizers, because the NLC polarizes the incident light and causes it to be reflected into the viewer 'in-phase' with its polarizing filter. The light reflected in-phase with the filter passes through the filter to the viewer, thus causing the surface to appear bright. When formulated properly, such materials can have a very sharp liquid-crystal to pure-liquid phase transition at a temperature referred to as the clearing temperature of the material. This behavior allows these materials to be used as micron-sized temperature indicators or hot-spot detectors, and forms the basis of operation for the invention.

Figure 1:
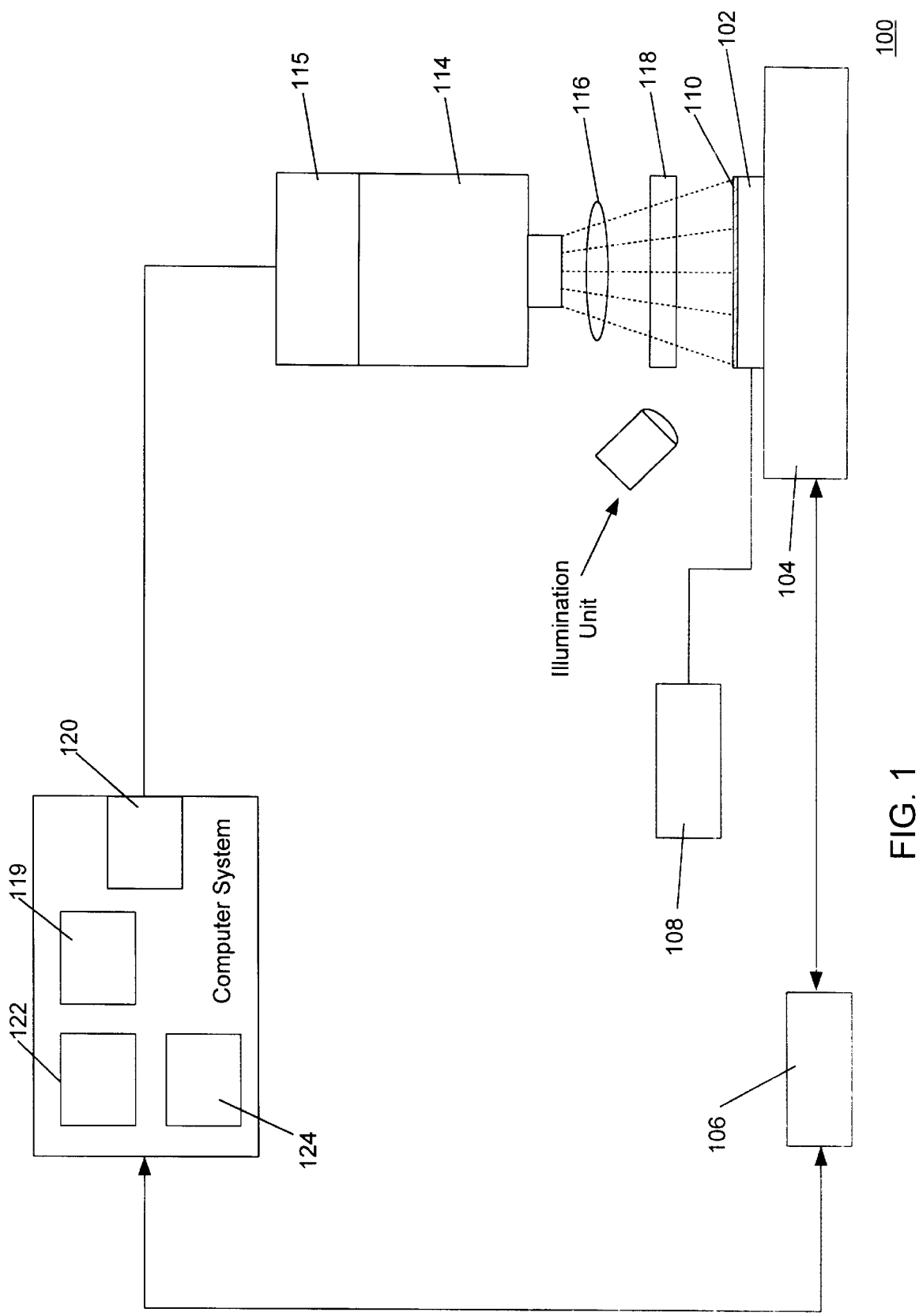
FIG. 1 shows a block diagram of temperature mapping system constructed according to the present invention.

FIG. 1 shows a block diagram of temperature mapping system 100 constructed according to one embodiment of the present invention. A device under test 102 (hereinafter referred to as DUT) is mounted on a temperature control platform 104. The DUT, for example can include an integrated circuit die or other electrical component. A temperature control unit 106 controls a temperature control platform 104 via electrical, thermal, or mechanical means, or via other means known to those skilled in the art. The DUT 102 is also electrically connected to a DUT probe unit 108, which provides power and/or control signals to the DUT 102. The surface of the DUT 102 is coated with the NLC material 110. An illumination unit may be used to illuminate the liquid crystal material 110 on the surface of the DUT 102, so as to provide a controlled, uniform source of light to be reflected from the NLC material 110. An optics element 114 receives light 116, which has been reflected and modified by the NLC material 110 and has passed through a crossed polarizer 118, to derive an image representative of the NLC coated surface. In one embodiment of the invention, the optics unit 114 includes a microscope, although those skilled in the art will realize that other optical assemblies may be used to receive the light 116 and derive an image. An optical/electrical conversion element 115 receives the image representative of the NLC coated surface and converts the image into an electrical signal. In one embodiment, the optical/electrical conversion element 115 may be a CCD camera, which converts the image into a series of digital data elements, although other methods of converting the image may be used.

In one embodiment of the invention a computer system, comprising a central processing unit 119 (hereinafter CPU), a frame grabber 120, an image processor 122 and a display unit 124 receives the digital data elements from the optics unit 114. In general, the CPU 119 coordinates processing functions within the computer system. One embodiment of the image processor 122 includes a software module executing on a commercial computer platform by way of a commercial operating system, although those skilled in the are will realize that other embodiments, such as an all-hardware signal processor or an application-specific hardware/software unit may be used. The frame grabber 120 receives the digital data elements which collectively represent the image from the microscope 114 and assembles the data elements into a frame format compatible with the subsequent image processing components.

The temperature control unit 106 and the temperature control platform 104 control (i.e., drive and maintain) the temperature of the DUT 102 through a range of temperatures which straddle the clearing temperature of the NLC material 110. As the temperature increases over time, the frame grabber 120 acquires and stores the sequence of images of the DUT 102, each at a temperature incrementally greater than the previous. The image processor 122 evaluates the sequence of stored images as described herein to generate a thermal map of the surface of the DUT 102.

In one embodiment, a hot-spot on the surface of the DUT 102 appears as a black spot on the surface of the object coated with the NLC material 110 in an otherwise light, undisturbed NLC background. The temperature of the black spot when it initially appears is the clearing temperature of the NLC material 110. As the substrate temperature of the surface rises, the black spot will grow in size due to the increase in the amount of the surface that is at or above the clearing temperature. By continuing to raise the substrate temperature, more of the surface can be made to appear black. Temperature mapping of the surface is accomplished by starting with a small black spot, and then carefully controlling and tracking the growth of the spot, coordinated with precise temperature control of the substrate. The illustrated form of the invention implements this methodology by synchronizing the acquisition of images of the NLC-coated surface with precise control of the substrate temperature.

In one embodiment, the method of generating a two dimensional graphic representation of the surface temperature of the object is based on the concept of a thermal test. The key component of a thermal test is its image sequence. The image sequence contains the NLC-coated surface images of the device, organized in an ordered sequence as a function of increasing substrate temperature over a precise temperature range. The image sequence also includes a priori information regarding the NLC clearing temperature of the NLC material 110 and a predetermined substrate temperature range. Temperature mapping begins by applying power to the DUT 102 mounted to the temperature control platform 104 and bringing the DUT 102 to a substrate temperature corresponding to a surface temperature that is just slightly below the level that allows the smallest hot-spot to be seen with the NLC material being used. Next, a digital image of the DUT is acquired and stored as the background data image. One embodiment of the invention includes interactive temperature stepping and image capture features to simplify these steps. The CPU 119 then coordinates automatic adjustment and control of the temperature of the temperature platform 104 and DUT 102, and acquires images of the device that show the outline of the hot-spot(s) growing as the temperature is raised and stabilized in increments of 0.1° C. steps, although lesser or greater temperature resolution may be used. When all of the images have been acquired, the CPU 119 and image processor 122 processes the image sequence via an image sequence processing interface and constructs a color-coded thermal map of the device's surface temperature distribution.

The image sequence processing interface is preferably equipped with interactive controls that allow a user to select only the images they want to process and to fine-tune the 'hot-spot' detection algorithm to extract the valid 'hot-spot' regions of the image sequence data while eliminating the background areas. The hot-spot detection algorithm is built around state-of-the-art image processing techniques which are specifically tailored to the many nuances of NLC based thermal mapping.

Figure 2:
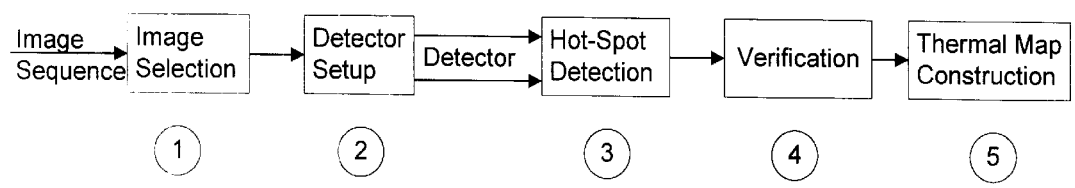
FIG. 2 shows flow diagram illustrating the temperature mapping and hot-spot detection algorithm; and, FIG. 3 illustrates the relative differences between the 4 neighbor model and the 8 neighbor model.

FIG. 2 shows flow diagram illustrating the temperature mapping and hot-spot detection algorithm.

The Process Variable Structures of the temperature mapping and hot-spot detection algorithm are given as follows:

Image Sequence:

$T_{min}$ = Auto-Acquisition START temperature
$T_{max}$ = Auto-Acquisition END temperature
$T_{cp}$ = Clearing temperature of the nematic liquid crystal (NLC). Temperature where a phase transition occurs within the material that causes it to radically alter the way it modulates incoming light.
$\Delta T$ = Auto-acquisition STEP temperature
BeginIndex = Image index to start processing from
EndIndex = Image index to end processing
Nimages = Total number of images that were acquired
ORIGINAL Image Array [1, NImages] = Array of the original acquired images
DATA Image Array [BeginIndex, EndIndex] = Array of processed images
Thermal Map Image = Image that will contain the composite thermal map of the DATA Image Array Detector:

Threshold Level = User-selectable (point-and-click) intensity level
Tolerance = Threshold level tolerance
Threshold Range = Intensity range that defines the hot-spot's signature (Threshold Level ± Tolerance)
Subtract Background? = Dictates whether to subtract a background image from the original image array, or not -continued

Figure 3:
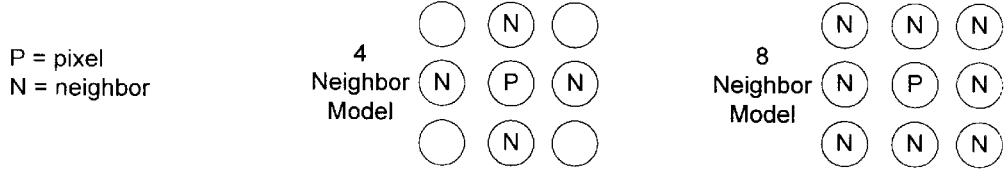

| | |
|---|---|
| Neighborhood = | Defines how to weigh the influence of a pixel's neighbors. Neighborhood processing may utilize 4 neighbor model or 8 neighbor model. FIG. 3 illustrates the relative differences between the 4 neighbor model and the 8 neighbor model. |

As shown in FIG. 2, one embodiment of the temperature mapping and hot-spot detection algorithm preferably comprises a sequence of five Process Steps. Each Process Step is described as follows:

1. Image Selection

This step allows the user to 'window-select' the images they want to process. It gives users the flexibility to properly process images that may have been acquired over a wider than necessary temperature range. Users will typically acquire additional images at higher and lower temperatures than they are truly interested in to ensure that the device's full thermal profile is acquired automatically. BeginIndex and EndIndex define the image indices for the 'true' minimum and maximum temperature images respectively that require processing.

2. Detector Setup

This is an important step of the process and the system is designed to provide the user with instant feedback on the settings he/she chooses. The main purpose of this step is to assist the user in properly defining the intensity 'signature' of valid hot-spot(s) that may be present in ORIGINAL Image Array. The parameters that make up the Detector process variable are used to practically describe and implement this signature for accurate processing.

3. Hot-Spot Detection

This step uses the Detector settings in combination with the following sub-steps to 'detect' the hot-spot regions in all of the window-selected images in ORIGINAL Image Array and stores the step-by-step results in DATA Image Array.

Sub-Step 1.

Smooth: This step implements a standard, North-South-East-West neighborhood weighted 3×3 Gaussian smoothing filter to smooth out the features of the images in ORIGINAL Image Array, although other smoothing filters, can be used.

Sub-Step 2.

Binarize: This step defines the intensity signature of valid hot spots in the selected images, preferably by 'binarizing' (pixel intensity values of 1 or 0 only) the images in DATA Image Array by setting all image pixels that fall within Threshold Range to a value of 1. Those pixels that fall outside of this range are set to a value of 0.

Sub-Step 3.

Clean: This step 'cleans' (eliminates unwanted and fictitious artifacts) the DATA Image Array images by preferably applying a 'low-pass spatial filter'. To provide even greater images the low-pass spatial filter is applied in combination with "n" consecutive 'erosions', wherein "n" is an integer, and in one embodiment is equal to three. The preferred process of low-pass spatial filtering combined with erosion of binary images allows small (in comparison to other structures present in the image) artifacts to be removed from the images without disturbing the contours of larger structures (i.e. hot-spots). This results in a very effective procedure to accurately detect and filter-out hot-spots in the type of images typically encountered with NLC-based thermal mapping applications.

4. Verification

The verification step is important to forcing the processed images to comply with the physics of NLC thermal mapping. In practical terms this means that in order for a candidate hot-spot pixel in an image to be considered 'real' the pixel at the same location in all subsequent images (i.e., higher temperature levels) must also have been detected. If not, then the pixel is considered to be non-real and should be discarded. This step implements this principle by running the images in DATA Image Array through a cascaded logical AND 'test'. The test checks the value of all detected hot-spot pixels (intensity equal to 1 at this stage) in all subsequent images. If the pixels pass the test then their intensity level of 1 is preserved else it is set to 0.

5. Thermal Map Construction

Since only supposed 'real' hot-spots pixels are present in DATA Image Array at this point and these pixels have unity intensity, construction of the Thermal Map is a straightforward procedure. The procedure begins by simply adding the images intensities together and storing the result in Thermal Map Image. With this, Thermal Map Image will have corresponding pixel intensity values that are exactly equal to the number of occurrences that the corresponding pixels were found to be valid in DATA Image Array. This simple (by design) fact can be exploited to efficiently assign temperature and color levels to the Thermal Map Image pixels, for example, using the following steps:

Sub-Step 1.

Temperature Relationship: Assign a temperature level to each image pixel using the following relationship:

$$T(\text{Intensity}) = T_{cp} + \text{Intensity} * \Delta T$$

Sub-Step 2.

Mask Creation: Create a temporary, binary mask image that has pixel intensity levels equal to 1 wherever the corresponding Thermal Map Image intensity is non-zero and zero everywhere else.

Sub-Step 3.

Image Multiplication: Now multiply the images from Sub-Steps 1 and 2 and assign this result to Thermal Map Image. This causes Thermal Map Image to have the proper temperature levels assigned to the hot-spot pixels and zero everywhere else.

Sub-Step 4.

Color Assignment: Use the standard rainbow color palette and adjust its range to correspond to the temperature range now present in Thermal Map Image (i.e. Red=Maximum and Blue=Minimum).

The ThermoMap Hot-Spot Detection Method consists of 4 steps:

1. Image selection
2. Detector setup
3. Hot-spot verification
4. Thermal map construction In summary, the preferred image selection allows the user to 'window-select' the minimum and maximum temperature images in the acquired image sequence to use for processing. In one embodiment the detector setup feature provides an interactive means for the user to specify the key parameters of the detection algorithm (intensity range, threshold, subtract background and neighborhood size) by clicking the mouse in the region that represents a 'valid' hot-spot. The user's selection is immediately shown by the software as a color highlight around the detected region of the selected image template. Once the user is satisfied with the results of the detector setup, in one embodiment the algorithm then goes on to process all the images in the sequence using the selected detector setup parameters. This step produces a binary image representation of the candidate hot-spot regions in the image sequence. Since the sequence was acquired with increasing substrate temperature, the sequence image will represent the GROWTH of the hot-spot regions in the images. This means that once a candidate hot-spot pixel in any image has been identified, for it to become a valid hot-spot pixel, it must remain a hot-spot pixel in all the subsequent image. With this in mind,, the detection algorithm quickly verifies this behavior in the image sequence by performing a cascaded logical AND of each image with those at higher temperature. Once this has been completed, the algorithm smooths the edges of the hot-spots using, for example, a 3×3 Gaussian smoothing filter, 'fills-in' these regions using the selected neighborhood, and then assigns an appropriate color and temperature to each region. The last step in the algorithm combines these validated images into a color/temperature coded composite thermal map.

It should be appreciated that various modifications can be made to the illustrated embodiments without departing from the scope of the invention. For example, while the illustrated embodiments have been described wherein the object is heated through a range of nominal temperatures from a relatively low nominal temperature limit below which the thermotropic material changes phase, to a relatively high nominal temperature limit above the temperature at which the thermotropic material changes phase, so that images can be acquired at incremental nominal temperatures within the range; other embodiments can be used wherein the object is cooled through a range of nominal temperatures from a relatively high nominal temperature limit above which the thermotropic material changes phase, to a relatively low nominal temperature limit below the temperature at which the thermotropic material changes phase, so that images can be acquired at incremental nominal temperatures within the range. In either event, the images can be stored and processed in succession of increasing incremental nominal temperatures as previously described; or processed in succession of decreasing incremental nominal temperatures wherein the steps of the various embodiments are essentially the same as described above, except that the step 4 entitled "verification" will be processed in a logically opposite manner.

Additional disclosure related to the invention is included in Appendix A, entitled *Users Guide to ThermoMap. Software Version 2.0, Rev A:06/97,*" and Appendix B, LabVIEW block diagrams for the ThermoMap Hot-Spot Detector.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of determining the location of hot spots on a surface of an object, comprising:

applying a thermotropic material to the surface of the object;

varying a nominal temperature of the object through a range of nominal temperatures between a first nominal temperature limit and a second nominal temperature limit, wherein one temperature limit is below and the other nominal temperature limit is above the temperature at which the thermotropic material changes phase;

acquiring a sequence of images of the surface, each of the images depicting a two dimensional temperature representation of the surface at a predetermined nominal temperature within the range of nominal temperatures, wherein each image in the sequence represents an incremental change in nominal temperature than that of a preceding image; and processing select ones of the images to define an intensity signature of valid hot spots in the select ones of the images and to determine the location of the hot spots on the surface as a function of the defined intensity signature.

2. A method according to claim 1, wherein the step of varying the nominal temperature of the object includes the step of varying the temperature of the object in incremental steps so that the object is stabilized at each of the nominal temperatures when each of the images of the surface are acquired.

3. A method according to claim 1, wherein the step of processing select ones of the images includes the step of selecting the images the user wishes to process to determine the hot spots.

4. A method according to claim 1, wherein the step of processing select ones of the images to define the intensity signature of valid hot spots includes the step of detecting potential hot spots in each of the select ones of the images.

5. A method according to claim 4, wherein each of the selected images is represented by a plurality of pixels, each of the pixels of a determinable intensity, and the step of detecting potential hot spots in each of the select ones of the images includes the step of binarizing a plurality of the pixels within each of the select images such that each pixel is designated as either a hot-spot pixel or a non-hot-spot pixel.

6. A method according to claim 5, wherein the step of detecting potential hot spots in each of the select ones of the images includes the step of applying a smoothing filter to a plurality of regions within each of the selected images prior to the step of binarizing the plurality of the pixels.

7. A method according to claim 5, wherein the step of detecting potential hot spots includes the step of applying a low-pass spatial filter to a plurality of regions within each of the images after the step of binarizing the plurality of the pixels.

8. A method according to claim 5, wherein the step of binarizing a plurality of pixels includes the steps of i) comparing each of the pixels to a predetermined threshold range and ii) designating each of the pixels as a hot-spot pixel if the pixel falls within the threshold range and designating the pixel as a non-hot-spot pixel if the pixel does not fall within the threshold range.

9. A method according to claim 1, wherein the step of processing select ones of the images includes the step of verifying each potential hot-spot.

10. A method according to claim 9, wherein the step of verifying each potential hot spot includes the steps of i) comparing consecutive images of the select ones in the sequence in which they are acquired, and ii) eliminating hot-spot pixels not having a hot-spot pixel at a corresponding location in an immediately succeeding image.

11. A method according to claim 9, wherein the step of verifying each potential hot spot includes the step of adding pixels from corresponding locations of each of the select images to produce a resulting pixel corresponding to an integer value representative of the number of images having hot-spot pixels at the corresponding location so as to produce the two dimensional graphic temperature representation.

12. A method according to claim 11, wherein the resulting pixel includes one of a plurality of integer values, each of an integer values corresponding to an assigned temperature and being represented by a predetermined color.

13. A method according to claim 1, further including the steps of:
maintaining the object at a first nominal temperature, and viewing the surface through a crossed polarizing filter and producing video data representative of a polarized image of the surface prior to the step of applying the thermotropic material.

14. A method according to claim 13, wherein the step of acquiring the sequence of images includes receiving and recording the polarized image at each of nominal temperatures so as to produce a time-series of images, and generating a thermal map of the surface from the time-series of images.

15. A method according to claim 14, wherein the step of varying the nominal temperature of the object through a range of nominal temperatures includes the steps of securing the object to a temperature control platform, and controlling the temperature of the object through the temperature control platform.

16. A method according to claim 14, wherein the step of viewing the surface further includes the steps of receiving and focusing light received from the surface, so as to form an image, and converting the image into a series of video data elements representative of the image.

17. A method according to claim 14, further including illuminating the thermotropic material applied to the surface for each of the images.

18. A method according to claim 14, wherein the step of acquiring the sequence of images includes:
receiving video data from an optics unit for each of the images;
forming the video data into a frame representative of the image; and
storing the video data of each of the frames so as to establish a data set representative of a time-sequence of the images.

19. A method according to claim 14, wherein the step of acquiring the sequence of images further includes:
receiving each of the images and generating map data representative of a thermal map of the surface corresponding to variations in consecutive frames of the images; and,
receiving the map data and displaying the two dimensional graphic temperature representation from the map data.

20. A method according to claim 14, further including the step of determining which of the images is selected for the step of processing, wherein the step of determining includes detecting the first image of the sequence that is determined to have a dark spot, and identifying a temperature corresponding to the first image, so as to determine the temperature at which the thermotropic material changes phase.

21. A system for determining the location of any hot spots on a surface of an object which has had a thermotropic material applied to the surface, comprising:
a temperature maintenance subsystem for varying a nominal temperature of the object through a range of nominal temperatures between a first nominal temperature limit and a second nominal temperature limit, wherein one temperature limit is below and the other temperature limit is above the temperature at which the thermotropic material changes phase;
an imaging subsystem for acquiring a sequence of images of the surface, each of the images depicting a two dimensional temperature representation of the surface at a predetermined nominal temperature within the range of nominal temperatures, wherein each image in the sequence represents an incremental change in nominal temperature than that of a preceding image; and
a processor for processing select ones of the images to define an intensity signature of valid hot spots in the select ones of the images and to determine the location of the hot spots on the surface as a function of the defined intensity signature.

22. A system according to claim 21, wherein the temperature maintenance subsystem includes means for varying the temperature of the object in incremental steps so that the object is stabilized at each of the nominal temperatures when each of the images of the surface are acquired.

23. A system according to claim 21, wherein the processor includes means for selecting the images the user wishes to process to determine the hot spots.

24. A system according to claim 21, wherein the processor includes means for detecting potential hot spots in each of the select ones of the images.

25. A system according to claim 24, wherein each of the selected images is represented by a plurality of pixels, each of the pixels of a determinable intensity, and the means for detecting potential hot spots in each of the select ones of the images includes the means for binarizing a plurality of the pixels within each of the select images such that each pixel is designated as either a hot-spot pixel or a non-hot-spot pixel.

26. A system according to claim 25, wherein the means for detecting potential hot spots in each of the select ones of the images includes means for applying a smoothing filter to a plurality of regions within each of the selected images prior to binarizing the plurality of said pixels.

27. A system according to claim 25, wherein the means for detecting potential hot spots includes means for applying a low-pass spatial filter to a plurality of regions within each of the images after binarizing the plurality of said pixels.

28. A system according to claim 25, wherein means for binarizing a plurality of pixels includes means for comparing each of the pixels to a predetermined threshold range and means for designating each of the pixels as a hot-spot pixel if the pixel falls within the threshold range and designating the pixel as a non-hot-spot pixel if the pixel does not fall within the threshold range.

29. A system according to claim 21, wherein the processor includes means for verifying each potential hot-spot.

30. A system according to claim 29, wherein the means for verifying each potential hot spot includes means for comparing consecutive images of the select ones in the sequence in which they are acquired, and means for eliminating hot-spot pixels not having a hot-spot pixel at a corresponding location in an immediately succeeding image.

31. A system according to claim 29, wherein means for verifying each potential hot spot includes means for adding pixels from corresponding locations of each of the select images to produce a resulting pixel corresponding to an integer value representative of the number of images having hot-spot pixels at the corresponding location so as to produce the two dimensional graphic temperature representation.

32. A system according to claim 31, wherein the resulting pixel includes one of a plurality of integer values, each of the integer values corresponding to an assigned temperature and being represented by a predetermined color.

33. A system according to claim 21, further includes:

means for maintaining the object at a first nominal temperature, means for viewing the surface through a crossed polarizing filter and producing video data representative of a polarized image of the surface prior to applying the thermotropic material.

34. A system according to claim 33, wherein the imaging subsystem includes means for receiving and recording the polarized image at each of a plurality of nominal temperatures so as to produce a time-series of images, and generating a thermal map of the surface from the time-series of images.

35. A system according to claim 34, wherein the temperature maintenance subsystem includes means for securing the object to a temperature control platform and controlling the temperature of the object through the temperature control platform.

36. A system according to claim 34, wherein the means for viewing the surface further includes means for receiving and focusing light received from the surface, so as to form an image, and converting the image into a series of video data elements representative of the image.

37. A system according to claim 34, further including means for illuminating the thermotropic material applied to the surface for each of the images.

38. A system according to claim 34, wherein the imaging subsystem includes:

means for receiving video data from an optics unit for each of the images;

means for forming the video data into a frame representative of the image; and means for storing the video data of each of the frames so as to establish a data set representative of a time-sequence of the images.

39. A system according to claim 34, wherein the imaging subsystem further includes:

means for receiving each of the images and generating map data representative of a thermal map of the surface corresponding to variations in consecutive frames of the images; and, means for receiving the map data and displaying the two dimensional graphic temperature representation from the map data.

40. A system according to claim 34, further including means for determining which of the images is selected for processing, wherein the means for determining includes means for detecting the first image of the sequence that is determined to have a dark spot, and means for identifying a temperature corresponding to the first image, so as to determine the temperature at which the thermotropic material changes phase.

* * * * *